United States Patent
Jaunet et al.

(10) Patent No.: US 10,413,758 B2
(45) Date of Patent: *Sep. 17, 2019

(54) METHOD FOR THE ADDITIVE MANUFACTURE OF A THREE-DIMENSIONAL OBJECT COMPRISING OR FORMING A COSMETIC COMPOSITION BY APPLICATION OF A PHOTOACTIVATABLE MATERIAL ONTO A POWDER, AND ASSOCIATED APPARATUS

(71) Applicant: L'OREAL, Paris (FR)

(72) Inventors: Clément Jaunet, Velizy Villacoublay (FR); Sonia Lorente Gonzalez, Vincennes (FR)

(73) Assignee: L'OREAL, Paris (FR)

( * ) Notice: Subject to any disclaimer, the term of this patent is extended or adjusted under 35 U.S.C. 154(b) by 186 days.

This patent is subject to a terminal disclaimer.

(21) Appl. No.: 15/501,454

(22) PCT Filed: Aug. 5, 2015

(86) PCT No.: PCT/EP2015/068082
§ 371 (c)(1),
(2) Date: Feb. 3, 2017

(87) PCT Pub. No.: WO2016/020447
PCT Pub. Date: Feb. 11, 2016

(65) Prior Publication Data
US 2017/0232675 A1    Aug. 17, 2017

(30) Foreign Application Priority Data
Aug. 5, 2014  (FR) ..................................... 14 57616

(51) Int. Cl.
| | |
|---|---|
| *A61Q 5/02* | (2006.01) |
| *B33Y 80/00* | (2015.01) |
| *B33Y 10/00* | (2015.01) |
| *B33Y 30/00* | (2015.01) |
| *A61Q 1/02* | (2006.01) |
| *A61K 8/02* | (2006.01) |
| *B29C 64/165* | (2017.01) |
| *A61Q 15/00* | (2006.01) |
| *A61Q 19/10* | (2006.01) |
| *B29L 31/00* | (2006.01) |

(52) U.S. Cl.
CPC ............... *A61Q 5/02* (2013.01); *A61K 8/022* (2013.01); *A61K 8/0237* (2013.01); *A61Q 1/02* (2013.01); *A61Q 15/00* (2013.01); *A61Q 19/10* (2013.01); *B29C 64/165* (2017.08); *B33Y 10/00* (2014.12); *B33Y 30/00* (2014.12); *B33Y 80/00* (2014.12); *A61K 2800/43* (2013.01); *A61K 2800/434* (2013.01); *A61K 2800/81* (2013.01); *B29L 2031/718* (2013.01)

(58) Field of Classification Search
CPC . A61Q 5/00; A61Q 1/02; B33Y 10/00; B33Y 30/00; B33Y 80/00; B29C 64/171; B29C 64/165; B29L 2031/718
See application file for complete search history.

(56) References Cited

U.S. PATENT DOCUMENTS

| | | | |
|---|---|---|---|
| 2002/0105114 A1* | 8/2002 | Kubo ................... | B29C 64/153 264/497 |
| 2009/0020920 A1 | 1/2009 | Kumagai et al. | |
| 2010/0304100 A1* | 12/2010 | Fong .................... | G03F 7/0037 428/205 |
| 2015/0366327 A1* | 12/2015 | LaHood, Sr. .......... | A45D 40/30 264/109 |
| 2016/0088920 A1* | 3/2016 | LaHood, Sr. ........ | A45D 33/006 264/255 |
| 2017/0232676 A1* | 8/2017 | Jaunet ................... | B33Y 10/00 264/308 |
| 2018/0186065 A1* | 7/2018 | Jaunet ................... | B33Y 80/00 |

FOREIGN PATENT DOCUMENTS

WO    WO-2014/039378 A1    3/2014

OTHER PUBLICATIONS

Terrence O'Brien, "Mink will let you 3D print custom makeup at home", May 27, 2014; Retrieved from the Internet: URL:http://www.engadget.com/2014/05/07/mink-will-let-you-3d-print-custom-makeup-at-home/.

* cited by examiner

Primary Examiner — Sanza L. McClendon
(74) Attorney, Agent, or Firm — Polsinelli PC (57) ABSTRACT

The method comprises the following steps:
(a) forming a powder layer (19) comprising at least one cosmetic powder;
(b) supplying a photoactivatable material on at least a first region of the layer (19);
(c) illuminating at least the first region of the layer (19) to activate the photoactivatable material;
(d) forming an additional powder layer (19) comprising at least one cosmetic powder;
(e) supplying a photoactivatable material on at least a second region of the additional layer (19);
(f) illuminating at least the second region of the additional layer (19) to activate the photoactivatable material;
(g) repeating steps (d) to (f) until the three-dimensional object is formed.

The cosmetic composition comprised in the three-dimensional object or forming the three-dimensional object can be restored after the three-dimensional object is formed.

20 Claims, 2 Drawing Sheets

METHOD FOR THE ADDITIVE MANUFACTURE OF A THREE-DIMENSIONAL OBJECT COMPRISING OR FORMING A COSMETIC COMPOSITION BY APPLICATION OF A PHOTOACTIVATABLE MATERIAL ONTO A POWDER, AND ASSOCIATED APPARATUS

CROSS REFERENCE TO RELATED APPLICATIONS

This application is a National Phase filing under 35 U.S.C. § 371 of PCT/EP2015/068082 filed on Aug. 5, 2015; and this application claims priority to Application No. 1457616 filed in France on Aug. 5, 2014 under 35 U.S.C. § 119. The entire contents of each application are hereby incorporated by reference.

This invention relates to a method for the manufacture of a three-dimensional object containing or forming a cosmetic composition The cosmetic composition contains at least one cosmetic product, in particular a makeup product, a care product, a washing product or a perfume, the cosmetic product being intended to be applied on a surface of the body of a user.

More generally, "cosmetic product" means in particular, in the sense of this invention, a product such as defined in Regulation (EC) no. 1223/2009 of the European Parliament and of the Council of Nov. 30, 2009 relating to cosmetic products.

According to the invention, the three-dimensional object advantageously forms a makeup powder, in particular an eye shadow, a foundation, a bronzer, or a blush, in the form of a simple powder, a hybrid powder or a wet powder. Alternatively, the three-dimensional object forms a deodorant and/or antiperspirant product, a soap, a solid shampoo or/and a solid perfume.

In order to manufacture a three-dimensional object comprising a cosmetic composition, it is known to use methods for forming such as molding, filling, compaction, multi-compaction, wet powder injection, extrusion, etc.

Such methods for manufacture impose constraints on the objects manufactured. In molding, the objects generally have a cutting limit, with a maximum undercut possible when they are molded, even in a flexible mold.

The methods of molding also limit the complexity of the shapes, since it is impossible to create a part in another, or to nest one part in another.

In all of the aforementioned methods, the height of the product is a limiting factor. Complex shapes, in particular three-dimensional are very difficult, and even impossible to create, and often very expensive. The methods for compacting, multicompacting and injecting slurry are also limited in terms of height of the finished product.

There are also limits in the coloring of the cosmetic composition, in particular in the number of colors that can be used, and in the control of the various colors in the cast mass. It is in particular tedious to create objects that have different colors and/or color shading, and/or graphic inscriptions, for example alphanumeric characters and/or juxtapositions of colors.

The aforementioned methods are also limited in the implementation of different precursor materials in order to form the cosmetic composition. It is for example tedious to create via the same method an object formed of cosmetic products of different natures and compositions.

Another difficulty results from the fact that the method of the aforementioned type are intended solely for the formation of the three-dimensional object.

In certain cases, it is necessary to prepare upstream of the formation at least one bulk, which complicates the manufacture in certain cases.

Moreover, when new objects integrating cosmetic compositions are developed, it is generally useful to create working models making it possible to determine the feasibility and the interest of the object.

These models are complex to create, and require many steps comprising the development of the formula, the manufacture of the bulk, the creating of a special tool, and product packaging or formation tests.

These tests sometimes have to be conducted several times before a satisfactory result is obtained, which increases development time and costs.

One aim of the invention is to provide a simple and versatile method for manufacturing three-dimensional objects comprising a cosmetic composition, with the objects able to have complex shapes, natures and appearances.

For this purpose, the invention relates to a method of the aforementioned type, the method comprising the following steps:

(a) forming a powder layer comprising at least one cosmetic powder;

(b) supplying a photoactivatable material on at least a first region of the layer;

(c) illuminating at least the first region of the layer to activate the photoactivatable material;

(d) forming an additional powder layer comprising at least one cosmetic powder, the additional layer at least partially covering the previous layer;

(e) supplying a photoactivatable material on at least a second region of the additional layer;

(f) illuminating at least the second region of the additional layer to activate the photoactivatable material;

(g) repeating steps (d) to (f) until the three-dimensional object is formed, the cosmetic composition comprised in the three-dimensional object or forming the three-dimensional object being recoverable after the three-dimensional object is formed.

The method according to the invention can include one or more of the following features, taken alone or in any technically possible combination:

the photoactivatable material comprises a photoinitiator and a photocrosslinkable compound suitable for activation by the photoinitiator.

the photocrosslinkable compound comprises at least one monomer, and/or at least one prepolymer and/or at least one polymer, particularly chosen from polyesters with unsaturation(s) or (meth)acrylate groups, polyurethanes and/or polyureas with (meth)acrylate groups, polyethers with (meth)acrylate groups, epoxyacrylates, polyorganosiloxanes with (meth)acrylate or (meth)acrylamide groups, perfluoropolyethers with acrylate groups, a polyene associated with a polythiol, the mixtures thereof or copolymers thereof.

the photoactivatable material is deposited in liquid form via a nozzle or printing head on the first region and/or on the second region.

depositing the photoactivatable material comprises positioning the nozzle or printing head in a succession of given positions on the first region and/or on the second region, and, in each given position, depositing a given quantity of photoactivatable material, illuminating the photoactivatable material deposited in the given position, and moving the nozzle or printing head to another given position on the first region and/or on the second region.

the illumination comprises positioning an advantageously coherent light source in regard to a succession of given points on the first region and/or on the second region, and for each given point, illuminating the photoactivatable material in the given position, and then moving the light source to another given position on the first region and/or on the second region.

the photoactivatable material is included in or forms a binding activator intended to bind at least one cosmetic powder.

at least one layer comprises a photoactivatable substrate material suitable for forming a substrate of the cosmetic composition, the substrate being non-recoverable, the method comprising illuminating the photoactivatable substrate material to form at least a part of the substrate.

the step (a) comprises the forming a plane powder layer comprising at least one cosmetic powder;

applying a powder binding activator and the binding of the powder in at least a first region of the powder layer;

step (e) comprising the formation of an additional plane powder layer comprising at least one cosmetic powder, the additional layer covering the previous layer;

the method comprising applying a powder binding activator on at least a second region of the additional powder layer, the photoactivatable material being advantageously contained in the binding activator.

a first binding activator supplied in the application step has a first color, a second binding activator supplied in the application step having a second color, the cosmetic composition formed comprising the first binding activator and the second binding activator on the same layer or on different layers.

it comprises the providing of a plurality of binding activators having different base colors, with the method comprising a step of forming at least one pixel of a layer having a predefined color by mixture of several binding activators of different base colors;

the binding activator is transparent or colored;

it comprises a step for depositing at least one ink from a printing cartridge on at least one powder layer formed in step (a) or in step (d).

the cosmetic powder contains fillers, pigments, colorants, polymers and/or fibers.

the method comprises the following steps:

defining a predetermined shape and/or color of a three-dimensional object;

determining the dimensions and local composition of the regions of each powder layer whereon a powder binding activator is to be applied, on the basis of the predetermined shape.

the three-dimensional object is chosen from a make-up powder, a hybrid powder, or a wet powder, a deodorant and/or antiperspirant powder product, a solid shampoo or soap powder.

the method comprises a preliminary step for determining characteristics of a color of an element using a color analysis device, determining the local composition of at least one region of a powder layer whereon the powder binding activator is to be applied being performed on the basis of the color characteristics determined using the color analysis device;

the three-dimensional object defines a hollow region comprising a powder not bound defined by a wall formed of cosmetic powder bound by at least one binding activator.

The invention also relates to an apparatus for the additive manufacture of a three-dimensional object comprising or forming a cosmetic composition, the apparatus comprising:

a substrate surface;

an assembly for forming successive layers comprising at least one cosmetic material and, for at least one layer, a photoactivatable material;

a source for illuminating the photoactivatable material;

a control unit, suitable for controlling the formation assembly, and the illumination source to perform the following steps:

(a) forming a powder layer comprising at least one cosmetic powder;

(b) supplying a photoactivatable material on at least a first region of the layer;

(c) illuminating at least the first region of the layer to activate the photoactivatable material;

(d) forming an additional powder layer comprising at least one cosmetic powder, the additional layer at least partially covering the previous layer;

(e) supplying a photoactivatable material on at least a second region of the additional layer;

(f) illuminating at least the second region of the additional layer to activate the photoactivatable material;

(g) repeating steps (d) to (f) until the three-dimensional object is formed, the cosmetic composition comprised in the three-dimensional object or forming the three-dimensional object being recoverable after the three-dimensional object is formed.

The device according to the invention can include one or more of the following features, taken alone or in any technically possible combination:

the light source is chosen from a lamp and a laser.

the formation assembly comprises at least one nozzle or printing head intended to dispense the photoactivatable material and/or at least one powder binding activator, the light source being suitable for moving in conjunction with the nozzle or printing head.

The invention will be easier to understand in view of the following description, provided solely as an example, and with reference to the appended drawings, wherein.

Figure 1:
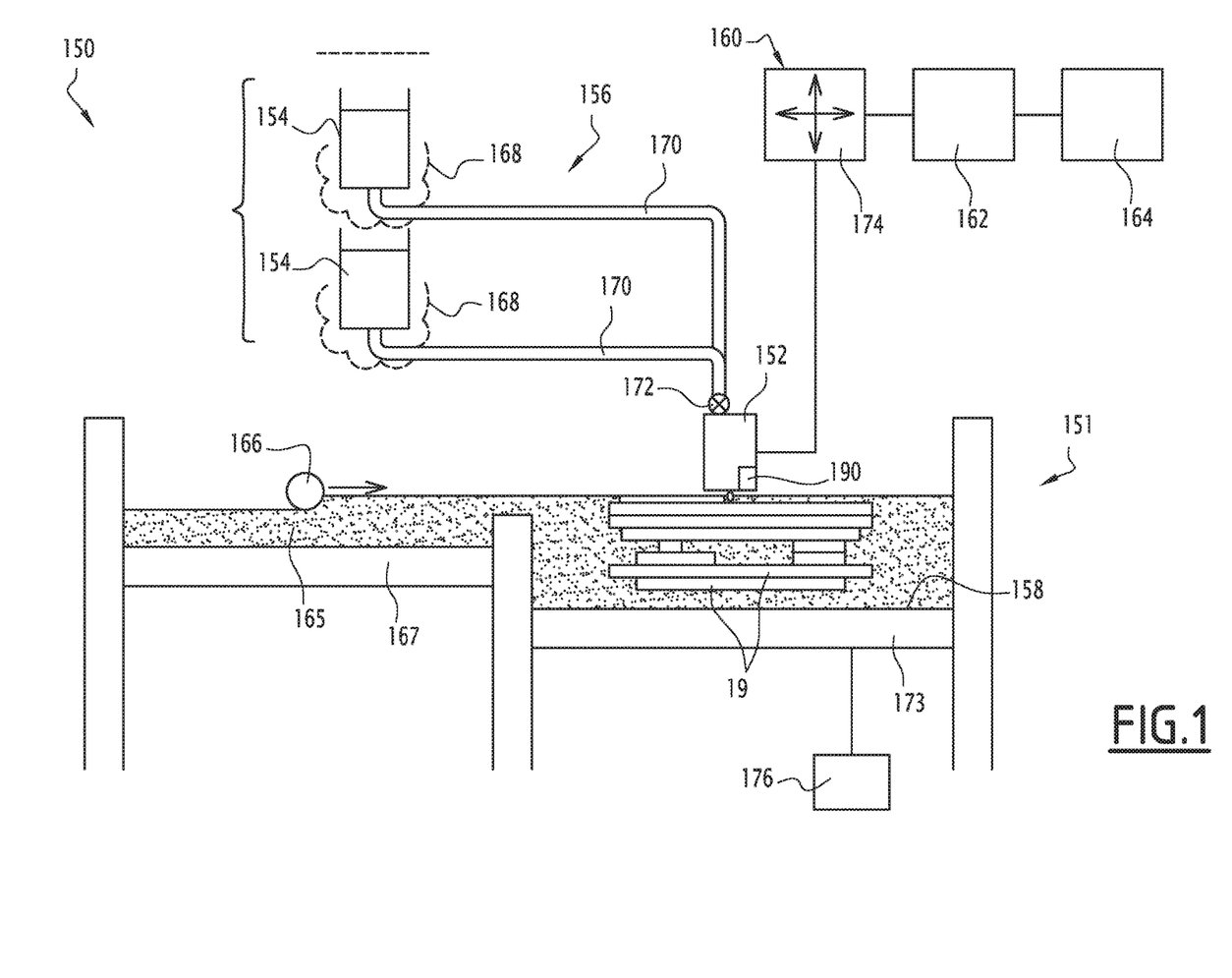
FIG. 1 is a diagrammatic view of an example of an apparatus, intended for the manufacture of a three-dimensional object comprising a cosmetic composition, by a method according to the invention.

This invention relates to a method for manufacturing three-dimensional objects 10 comprising a cosmetic composition 12 or formed from a cosmetic composition 12, using an apparatus for manufacturing by depositing binder onto powder, of which an example is shown in FIG. 1.

Figure 2:
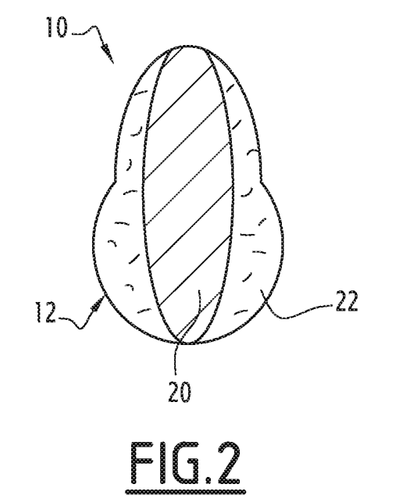
FIGS. 2 to 4 show examples of three-dimensional objects created by a method according to the invention, using the apparatus of FIG. 1.
Figure 4:
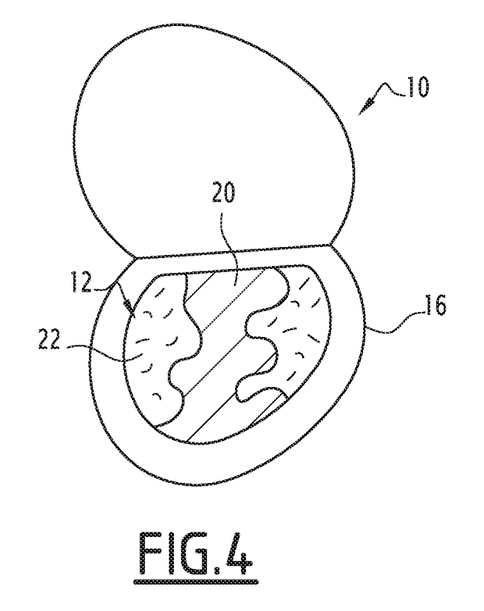

The method according to the invention is intended to manufacture three-dimensional objects 10 formed of a cosmetic composition 12, such as shown for example in FIG. 2 to be provided directly to the user or to be inserted into a separately manufactured packaging 16 of the cosmetic composition 12 such as shown in FIG. 4.

Figure 3:
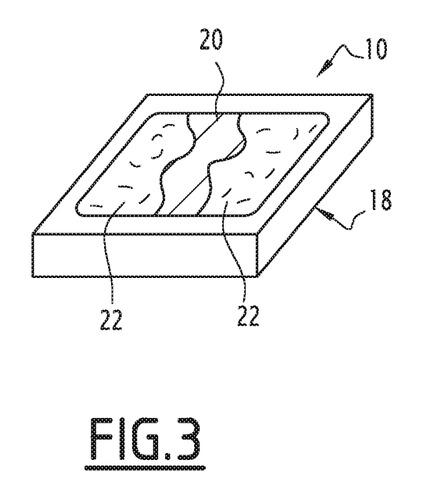

In an alternative, shown in FIG. 3, the method according to the invention is also intended to manufacture by additive deposit three-dimensional objects 10 comprising, in addition to the cosmetic composition 12, a substrate 18 bearing the cosmetic composition 12, the substrate 18 being manufactured simultaneously by additive deposit with the cosmetic composition 12.

According to the invention, the cosmetic composition 12, and if applicable the substrate 18, are formed of a plurality of successive layers 19 formed using at least one photoactivatable material, deposited on each other.

The cosmetic composition 12, and if applicable the substrate 18, are formed of a plurality of successive layers 19 each comprising at least one powder and at least one local binding activator of the powder, with layers 19 deposited on each other, the photoactivatable material being included in the binding activator or forming the binding activator.

The photoactivatable material is therefore included in or forms a photoactivatable binder intended to bind at least one cosmetic material, in particular a powder.

Advantageously, the photoactivatable material comprises at least one photoinitiator and at least one photocrosslinkable compound suitable for activation by the photoinitiator.

The photocrosslinkable compound generally comprises one or a plurality of polymers and/or prepolymers comprising double ethylene-polymerizable bonds, and/or one or a plurality of double bond reactive monomers.

Double bond reactive monomers, when they are present, are generally one or a plurality of vinyl monomers, for example acrylates or methacrylate, in particular acrylic or methacrylic acid esters.

Each reactive monomer comprises at least one double ethylene bond, and preferably several double ethylene bonds.

The polymer or polymers and/or prepolymers comprising double ethylene bonds have an average number of double ethylene bonds per polymer molecule greater than 1.

As examples of photocrosslinkable polymers and prepolymers that can be used in the photocrosslinkable compound, mention may be made of:
  polyesters with unsaturation(s); this is a group of polymers of the polyester type that has one or a plurality of double ethylene bonds, distributed at random in the main chain of the polymer.
  polyesters with lateral and/or terminal (meth)groups obtained by means of polycondensation of a mixture of linear or branched or cycloaliphatic aliphatic dicarboxylic acids, of linear or branched or cycloaliphatic aliphatic diols;
  polyurethanes and/or polyureas with (meth)acrylate groups, obtained by means of polycondensation of cycloaliphatic and/or aromatic aliphatic diisocyanates, triisocyanates and/or polyisocyanates, of at least one (meth)acrylic acid ester et of one diol or polyol, of polyols, in particular of diols, free from ethylene-polymerizable unsaturations, and of at least one (meth) acrylic acid ester and of a diol or polyol;
  polyethers with (meth)acrylate groups obtained by means of esterification, by (meth)acrylic acid, terminal hydroxyl groups of homopolymers or of copolymers of C1-4 alkylene glycols;
  epoxyacrylates obtained by means of a reaction between at least one diepoxide and one or a plurality of carboxylic acids or carboxylic polyacids comprising at least one double ethylene bond;
  polyorganosiloxanes with (meth)acrylate or (meth)acrylamide groups obtained respectively by means of esterification, advantageously by (meth)acrylic acid, polyorganosiloxanes, and by amidification, for example by (meth)acrylic acid, of polyorganosiloxanes carrying lateral and/or terminal primary or secondary amine groups;
  perfluoropolyethers with acrylate groups obtained by means of esterification, for example by (meth)acrylic acid, of perfluoropolyethers carrying lateral and/or terminal hydroxyl groups;
  a polyene such as defined hereinabove associated with a polythiol;
  mixtures or copolymers thereof.

The photoinitiator or photoinitiators that can be used in the photoactivatable material of this invention are described, for example in the following articles of which the content is an integral part of this application: "Les photoinitiateurs dans la réticulation des revêtements", G. Li Bassi, Double Liaison—Chimie des Peintures, No. 361, November 1985, pages 34-41; industrielles de la polymérisation photoinduite", Henri Strub, L'Actualité Chimique, February 2000, pages 5-13; and "Photopolymeres: théoriques et réaction de prise", Marc, J. M. Abadie, Double Liaison—Chimie des Peintures, No. 435-436, 1992, pages 28-34.

These photoinitiators include the alpha-hydroxyketones, alpha-aminoketones, chloroacetophenones, aromatic ketones, thioxanthones and quinones, benzoin ethers, acylphosphine oxides, and copolymerizable photoinitiators.

Copolymerizable photoinitiators are molecules comprising both a photoinitiator group capable of photoinduced radical splitting and at least one double ethylene bond.

The radiation suitable for the crosslinking of the cosmetic compositions according to the present invention has a wavelength between 210 and 600 nm, preferably between 250 and 400 nm.

In one preferred embodiment of the invention, a UV lamp and particularly a mercury vapor lamp, optionally doped with further elements, such as gallium, suitable for modifying the emission spectrum of the light source, is used. Alternatively or in addition, a laser is used to cause the crosslinking.

The cosmetic composition 12, and if applicable the substrate 18, are formed of a plurality of successive layers 19 each comprising at least one powder and at least one local binder of the powder, with layers 19 deposited on each other.

In this example, the binder forms as such a powder binding activator. Alternatively, a portion of the binder is dispersed in powder form in the powder and is activated by an activator added subsequently into the mix of binder and powder.

Advantageously, several different binders are used to form the cosmetic composition, by being deposited within the same layer or in different layers.

The different binders have for example different compositions, in order to form, within the cosmetic composition 12, regions 20, 22 with a different composition and/or appearance, for example in terms of chemical nature, mechanical properties and/or colors, as shown for example in FIG. 6 or 7, or shadings of composition and of color.

In particular, different binders have different colors. These colors are in particular base colors (for example black, yellow, cyan, magenta) making it possible to create via mixing a complete range of different colors.

Alternatively, the binder or binders have a monochrome color, or an absence of color. The color of each point of the cosmetic composition is then provided by spraying droplets of an ink or of several inks of different colors coming from one or a plurality of printing cartridges.

The thickness of each layer 19 forming the three-dimensional object 10 is for example less than 1 mm and is in particular between 50 microns and 200 microns.

Each layer 19 comprises at least one filled area formed of at least one powder and of at least one binder of the powder. Optionally, each layer 19 comprises empty areas defined by adjacent filled areas, according to the desired shape of the three-dimensional object 10.

At ambient temperature, for example at 25° C., the cosmetic composition is structured. "Structured" means in particular, in the sense of this invention, that the cosmetic composition has its own mechanical resistance, i.e. it spontaneously retains its shape, throughout the entire lifetime of the product in the absence of external stress. This lifetime is for example at least one day, and in particular at least one year.

As such, the cosmetic composition in the three-dimensional object formed at the end of the method according to the invention is not liquid at ambient temperature, and does not spontaneously flow in a macroscopically visibly manner for the entire duration of the life of the product, in the absence of external stress. This lifetime is for example at least one day, and in particular at least one year.

Preferably, the cosmetic composition is solid. In this case, it can be grasped and moved by the user, without flowing.

According to the invention, the cosmetic composition is recoverable. "Recoverable" means in particular, in the sense of this invention, that at least a portion of the cosmetic composition can be applied on a body surface of the user and that the composition is capable of being at least partially detached from the three-dimensional object in order to remain on the body surface.

In particular, the crosslinking supplied by the photoactivatable material is not total and does not prevent the cosmetic material from being restored.

Advantageously, the cosmetic composition is recoverable by friction between the body surface and the cosmetic composition, without physical deterioration of the body surface. Alternatively, the cosmetic composition is recoverable by friction between an applicator and the cosmetic composition.

In one alternative, the cosmetic composition is recoverable by soaking in a biologically compatible liquid in order to at least partially detach it from the three-dimensional object and apply it on the body surface.

In one alternative, the cosmetic composition can be restored by prior heating of the three-dimensional object at a biologically compatible temperature, for example less than 60° C.

The cosmetic composition is preferably deliquescent, i.e. a portion of the powder, optionally carrying binder is able to be detached from the rest of the cosmetic composition under the effect of a mechanical action.

Advantageously, the cosmetic composition is chosen from a colored cosmetic composition, and in particular a makeup composition for the skin and/or mucosa.

The cosmetic composition is for example in the form of a makeup powder, a hybrid powder or a wet powder.

Alternatively, the three-dimensional object forms a deodorant and/or antiperspirant product, a soap, a solid shampoo or/and a solid perfume.

In particular such a composition can be a foundation, a blush, a powder, a blusher or eye shadow, an anti-wrinkle compound, a lipstick or a lip gloss, optionally having care or treatment properties.

This can be a colored makeup composition (beige or green) intended to correct the color of the foundation.

A composition according to the invention can also form a makeup composition or nail or eyelash care.

The powder present in the cosmetic composition advantageously has an average particle size between for example 0.1 μm and 150 μm, preferably between 0.1 μm and 100 μm. Equipment making it possible to take this measurement is the "Mastersizer 3000" from Malvern, such as described in U.S. Pat. No. 6,778,271 or in GB2340932.

This technique consists in measuring the intensity of the light diffused during the passage of a laser beam through a sample of dispersed particles. This data is then analyzed in order to calculate the size of the particles that created the diffraction image.

It can be used for the liquid process and the dry process. The choice of the method depends on the powder to be analyzed. Those skilled in the art use the module that corresponds to the method chosen and take the measurement.

These grains can be spheroids or particles of irregular shape, and have a size between 0.1 microns and 100 microns.

The cosmetic powder mass content in the cosmetic composition, after forming the three-dimensional object, is greater than 40%, in particular greater than 85%, advantageously greater than 90%.

In the case of a makeup powder, the cosmetic powder mass content is greater than 80%, and is in particular between 85% and 95%.

In the case of a hybrid powder, the cosmetic powder mass content is advantageously between 60% and 90%.

The powder comprises for example fillers, polymers, pigments and/or fibers.

The term "fillers" should be understood for the purposes of the invention to denote inorganic or synthetic colorless or white particles of any shape, insoluble in the medium of the composition regardless of the temperature at which the composition is manufactured. These fillers may particularly be used to modify the rheology or texture of the composition.

The fillers may be mineral or organic particles of any shape, in sheet, spherical or oblong form, regardless of the crystallographic shape (for example sheet, cubic, hexagonal, orthorhombic, etc). Mention may be made of talc, mica, silica, kaolin, polyamide, poly-β-alanine and polyethylene powders, tetrafluoroethylene polymer powders, lauroyl-lysine, starch, boron nitride, polymeric hollow microspheres such as those of polyvinylidene chloride/acrylonitrile of acrylic acid copolymers and silicone resin microbeads, elastomer polyorganosiloxane particles, precipitated calcium carbonate, magnesium carbonate and hydro-carbonate, hydroxyapatite, hollow silica microspheres, glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate.

This can also be particles containing a copolymer, said copolymer comprising trimethylol hexyllactone. In particular, it may be a copolymer of hexamethylene diisocyanate/trimethylol hexyllactone.

The powder can comprise generally spherical particles of at least one surface-stabilized polymer, in particular in the form of nanoparticles of polymers. The nanoparticles are preferably of a size between 5 nm and 600 nm.

Radical polymers, polycondensates, and even polymers of natural origin can as such be used. The polymer can be chosen by those skilled in the art according to its properties, according to the subsequent application desired for the composition.

As such, the polymer can be film-forming or non-film-forming; in this second case, it can in particular have the form of a crosslinked polymer.

It is therefore possible to use film-forming polymers, preferably having a low glass transition temperature (Tg), less than or equal to ambient temperature.

It is also possible to use non-film-forming polymers, optionally crosslinked, which can be used as fillers dispersed in a stable manner in an oil.

The polymers that can be used in the context of this invention preferably have a molecular weight of about 2,000 to 10,000,000, and a glass transition temperature of −100° C. to 300° C. When the polymer has a Tg that is too high for the desired application, it can be combined with a plasticizer so as to lower the Tg of the mixture used. The plasticizer can be chosen from the standard plasticizers used in the field of application and in particular from the components that can be solvents of the polymer.

Of the crosslinked film-forming polymers, mention may be made of radical, acrylic or vinyl homopolymers or copolymers, preferably with a Tg less than or equal to 30° C. Of the non-film-forming polymers, mention may be made of radical, vinyl or acrylic homopolymers or copolymers, optionally crosslinked, preferably having a Tg greater than or equal to 40° C., such as methyl polymethacrylate, polystyrene or tert-butyl polyacrylate.

The pigments are chosen for example from organic pigments, mineral pigments and nacres.

The term "nacres" should be understood to mean iridescent or non-iridescent colored particles of any shape, which are in particular produced by certain mollusks in their shell or else are synthesized and which exhibit a color effect by optical interference.

The nacres may be selected from pearlescent pigments such as titanium mica coated with iron oxide, titanium mica coated with bismuth oxychloride, titanium mica coated with chromium oxide, titanium mica coated with an organic dye, and pearlescent pigments based on bismuth oxychloride. This may also involve mica particles at the surface whereof are superposed at least two successive layers of metal oxides and/or of organic dyes.

By way of example of nacres, mention may also be made of natural mica coated with titanium oxide, with iron oxide, with natural pigment or with bismuth oxychloride.

The nacres may more particularly possess a yellow, pink, red, bronze, orange, brown, gold and/or copper color or glint.

The fibers are chosen for example from polyamide fibers such as nylon fibers.

The binder mass content in the cosmetic composition is preferably between 5% and 60%.

In the case of a makeup powder, this mass content is advantageously between 5% and 15%. In the case of a hybrid powder, the binder mass content is advantageously between 10% and 40%.

Advantageously, the binder is able to bind the powder by simple contact with the powder and/or after crosslinking, when the binder comprises or forms a photoactivatable material such as defined hereinabove.

The binder is then at least partially liquid at ambient temperature, for example 25° C.

By "at least partially liquid" we generally mean that the binder is able to flow under the effect of its own weight. In particular, the binder is able to flow through an extrusion nozzle or a printing head.

An extrusion nozzle is a basic element for dosing, for example cylindrical. A printing head is an element of a printer in charge of spraying drops of ink. A printing head comprises a multitude of nozzles.

In general, the spraying of drops in a printing head is caused by an active means of movement, such as a piezoelectric element.

The "at least partially liquid" binder is entirely liquid, or comprises a liquid phase in which are dispersed solid elements, which flow by the intermediary of the liquid phase.

Advantageously, the binder is deposited in the form of droplets of liquid which are sprayed using a nozzle or printing head onto a layer of powder devoid of binder.

The viscosity of the binder, taken at its depositing temperature on the nozzle or printing head is for example less than 5 mPa·s and in particular between 0.5 mPa·s and 3 mPa·s.

In one alternative, the binder is at least partially in liquid form under heat.

It is for example intended to be heated in order to be deposited in liquid form in a layer of powder, then to at least partially solidify, after it is deposited in a layer of powder, and/or after crosslinking, when the binder comprises or forms a photoactivatable material such as defined hereinabove.

"Under heat" means in particular above the melting point of the binder.

For the purposes of the invention, the melting temperature is the temperature of the most endothermic peak observed in thermal analysis (DSC), such as described in ISO standard 11357-3: 2011.

In this embodiment, the at least partially liquid binder is able to at least partially solidify by cooling and/or by crosslinking.

By "at least partially solidify" we mean that the binder is able to be structured, in the sense defined hereinabove. In particular, the viscosity of the binder is able to increase. In particular, the binder is able to become solid.

The cooling advantageously changes the binder to a temperature less than the temperature that it had when it was deposited. This temperature is preferably less than the melting point of the binder.

The temperature loss of the binder during cooling is greater than 3° C., in particular greater than 5° C.

Alternatively, the binder can be activated by solvent evaporation.

In a first embodiment, the binder comprises a main binding agent intended to give a structure to the powder. It advantageously comprises a secondary binding agent in addition to the main agent. It also comprises a photoactivatable material such as defined hereinabove.

In a second embodiment, a first binder comprises a main binding agent intended to give a structure to the powder. It advantageously comprises a secondary binding agent in addition to the main agent.

A second binder is formed of a photoactivatable material such as defined hereinabove. In this case, the first binder and the second binder are deposited on the same layer of powder in the same positions or in different positions.

The main binding agent is preferably chosen from oils, particularly silicone oils, or esters.

Mention can as such be made of hydrocarbon oils such as paraffin oil or petroleum jelly or vaseline; mink oil, tortoise oil, soybean oil, perhydrosqualene; sweet almond oil, calophyllum oil, palm oil, grape seed oil, sesame oil, corn oil, rapeseed oil, sunflower oil, cotton oil, castor, avocado, jojoba, olive oils or germs of cereals; esters of lanolin acid, of oleic acid, of lauric acid, of stearic acid; fatty esters, such as lisopropyl myristate, isopropyl palmitate, butyl stearate, hexyl laurate, diisopropyl adipate, isononyl isononanoate, 2-ethylhexyl palmitate, 2-hexyl decyl laurate, 2-octyldodecyl palmitate, 2-octyldodecyl myristate or lactate, 2-diethylhexyl succinate, diisostearyl malate, glycerin or diglycerin triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleic alcohol, linoleic alcohol or linolenic alcohol, isostearyl alcohol or octyl dodecanol; silicone oils such as PDMS, optionally phenylated such as phenyltrimethicones or optionally substituted with aliphatic and/or aromatic groups, optionally fluorinated, or with functional groups such as hydroxyl, thiol and/or amine groups; polysiloxanes modified by fatty acids, fatty alcohols or polyoxyalkylenes, fluorinated silicones, perfluorinated oils. Volatile oils can also be used, such as cyclotetradimethylsiloxane, cyclopentadimethylsiloxane, cyclohexadimethylsiloxane, methylhexyldimethylsiloxane or isoparaffins such as 'ISOPARs', in particular isododecane.

The or each binder contained in the cosmetic composition, forms a network for maintaining the composition, in particular the powder contained in the composition. This network breaks on the surface during the application of the cosmetic product, allowing for the restoration of the composition.

The additional agent is chosen from water, an alcohol, in particular methanol, ethanol, propanol, a polymer, in particular a polyvinyl alcohol, or a polymer resin, a ceramic precursor, such as a polycarobisilazane or a mineral precursor, in particular with a silica base.

The manufacturing method according to the invention is implemented in an apparatus 150 via the manufacture by deposit of binder on successive layers of powder, of which an example is diagrammatically shown in FIG. 1.

The apparatus 150 comprises a formation assembly 151 of successive layers of powder.

The apparatus 150 comprises at least one nozzle or printing head 152 intended for the distribution of at least one powder binding activator in liquid form, and, for each binding activator distributed by the nozzle or printing head 152, a container 154 for the packaging of the binding activator, and a conveying assembly 156 of the binding activator between the container 154 and the nozzle or printing head 152.

For example, when several binding activators for different colors are used, the apparatus 150 advantageously comprises a nozzle or printing head per color.

The apparatus 150 comprises a substrate surface 158, able to carry the successive layers of powder, and an assembly 160 of relative displacement of the nozzle or printing head 152 with respect to the substrate surface 158.

The apparatus 150 also comprises a control unit 162 for the formation assembly 151, for the displacement assembly 160 and for the conveying assembly 156. It advantageously comprises a man-machine interface 164.

According to the invention, the apparatus 150 comprises a source 190 of radiation able to activate the photoactivatable material present in each layer 19 that contains it.

The source of radiation 190 is for example mobile jointly with the nozzle or printing head 152, and being advantageously carried by the nozzle or printing head 152. In this case, The source of radiation 190 is preferably able to be activated by pulses before each displacement of the nozzle or printing head 152 between two positions opposite the layer 19 being formed.

As indicated hereinabove, the source 190 is able to emit a suitable radiation for the crosslinking at a wavelength between 210 and 600 nm, preferably between 250 and 400 nm.

In one embodiment of the invention, the source 190 is a UV lamp and particularly a mercury vapor lamp, optionally doped with further elements, such as gallium, suitable for modifying the emission spectrum of the light source 190.

Alternatively or in addition, the source 190 comprises a laser suitable for moving in conjunction with the nozzle or printing head 152 or which can be moved independently of the nozzle or printing head 152.

It is as such able to irradiate the photoinitiator at a suitable wavelength for its decomposition or/and to cause a local heating of the binder generating a thermal decomposition of the photoinitiator.

The formation assembly 151 comprises a powder container 165, and a member for dispensing powder 166 to the substrate surface 158 or to a previous layer of powder 19.

In the example shown in FIG. 1, the powder container 165 is defined downwards by a mobile piston 167, able to move upwards in order to maintain the level of powder in the container 165, after application of a layer 19.

The member for dispensing powder 166 here comprises a movably mounted roller in the container 165, on the upper surface of the powder, in order to push a layer of powder laterally with regards to the substrate surface 158, directly on this surface 158, or on a previous layer of powder 19 carried by the substrate surface 158.

Each layer of powder 19 formed as such is as such plane. It is devoid of macroscopic relief of a height greater than 4 times the average thickness of the layer 19.

The average thickness of the layer of powder 19 is less than 1 mm and is generally between 50 microns and 200 microns.

In this example, the apparatus 150 comprises at least one nozzle or printing head 152 that distributes a plurality of different binding activators, obtained from several respective containers 154.

The nozzle or printing head 152 defines at least one dispensing orifice of the binding activator. Advantageously, it is able to distribute the binding activator in the form of successive droplets which are sprayed towards the substrate surface 158 on a layer of powder 19 that has just been deposited.

Each droplet preferably has a mass less than 100 ng, and is for example between 30 ng and 100 ng. The distance separating the dispensing orifice of the layer of powder 19 is preferable less than 5 mm, and is in particular between 0.5 mm and 1.5 mm.

As such, each droplet or set of droplets sprayed in a given position of the nozzle or printing head 152 is able to define an area of the layer 19 forming a "pixel" on the layer of powder 19. The composition and/or appearance of each pixel, in particular its color, can as such be defined by the nature of the binding activator or activators added in the pixel.

In the particular case where the binder is a liquid under heat, each container 154 is advantageously provided with a heating system 168 able to maintain the binding activator in liquid form in the container 154.

The conveying assembly 156 comprises a duct 170 for the intake of binding activator, connecting the container 154 to the nozzle or printing head 152, a system (not shown) for pumping the binding activator through the duct 170, and advantageously at least one control element 172 for the flow of the binding activator cosmetic material flowing through the intake duct 170, controlled by the unit 162.

The control element 172 is for example a valve controlled between a configuration for blocking the flow of the binding activator and a configuration for the distribution of the binding activator.

In one alternative, the conveying assembly 156 is devoid of a control element 172, with the flow of the cosmetic material being controlled by the pumping system.

In the particular case where the binder is a liquid under heat, the each duct 170 and the nozzle or printing head 152 are thermally insulated in order to maintain the binding activator in liquid form during its conveying.

In this example, the substrate surface 158 is defined on a vertically movable piston 173. After the forming of each layer 19, and the application of a binding activator in at least one region of the layer 19, the piston 173 is able to be moved downwards, in order to lower the layer 19 that has just been formed under the upper surface of the powder present in the container. This allows for the application of another layer of powder devoid of binding activator on the one that has just received the binding activator through the intermediary of the member for dispensing powder 166.

The displacement assembly 160 is able to allow for the relative positioning according to three axes of the nozzle or printing head 152 with respect to the substrate surface 158, or with respect to the previous layer 19 deposited on the substrate surface 158.

The displacement assembly 160 is controlled by the unit 162 in order to horizontally displace the nozzle or printing head 152 with respect to the previous layer 19 or with respect to the substrate surface 158, in order to selectively deposit at least one droplet of binding activator at a predetermined location on the layer being formed, corresponding to a pixel such as defined hereinabove.

The displacement assembly 160 is furthermore controlled by the unit 162 in order to vertically maintain the vertical distance between the nozzle or the printing head 152 and the support surface 158 or the previous layer.

In this example, the displacement assembly 160 comprises a mechanism 174 for the three-dimensional displacement of the nozzle or printing head 152, and a mechanism 176 for the vertical displacement of the substrate surface 158.

The control unit 162 is able to calculate, using a digital model of the three-dimensional object, the spatial arrangement of the binding activator within each layer of powder 19 to deposit it using each nozzle or printing head 152, and, within each layer 19 to be formed, the exact composition of each area of the linking activator in each area of the layer 19.

On this basis, the control unit 162 is able to control the corresponding relative displacement of each nozzle or printing head 152 in relation to the substrate surface 158 in order to deposit a given binding activator onto each zone to be formed of each layer 19, and control the controlling of the conveying assembly 156, in particular the pumping system and the control element 172, at each position of the nozzle or printing head 152, according to the activator desired in this area.

The man-machine interface 164, when it is present, is able to allow a user to define the shape of a three-dimensional object to be create, for example by selection of a digital model file in a database of digital models, or by importing a predefined digital model file, with a view to its use by the control unit 162.

An example method for producing according to the invention will now be described.

Advantageously, the user initially defines using the man-machine interface 164 the shape of the composition of the object to be created, by example by choosing a digital model file in the database of digital models or by importing this file.

Then, the digital model file is sent to the control unit 162. The control unit 162 then defines the shape of the different layers 19 intended to form the three-dimensional object, and within each layer the composition in binding activator of each area of the layer defining a "pixel".

The control unit 162 then calculates the displacement required for the or each nozzle or printing head 152 during the construction of each layer 19, and determines if a binding activator must be added at a given position of the nozzle or binding activator 152 and where applicable, what activator(s) must be added at each given position of the nozzle or binding activator 152.

Each binding activator is prepared in a container 154. At least one container 154 then contains a binding activator comprising at least one binder.

According to the invention, at least one binder comprises photoactivatable material such as defined hereinabove. Alternatively, at least one binder is formed of a photoactivatable material such as defined hereinabove.

Then, the control unit 162 controls the formation assembly 151, displacement assembly 160 and the conveying assembly 150 based on the calculations made previously in order to successively form the various layers 19 on each other.

For each layer 19 to be formed, the control unit 162 first controls the formation assembly 151 in order to deposit a layer of powder with respect to the previous layer 19 or the substrate surface 158 where applicable. The layer of powder is plane and is devoid of binder.

The control unit displaces the nozzle or printing head 152 in each area to be formed of the layer 19 and sprays at least one binding activator, advantageously in the form of liquid droplets, against the layer of powder 19 that has just been deposited.

The droplets are sprayed directly on the layer of powder 19 or against the substrate surface 158.

During this operation, the control unit 162 substantially maintains constant the vertical distance between the nozzle or printing head 152 and the previous layer 19 and/or the substrate surface 158.

In a first embodiment, between each displacement of the nozzle or printing head 152 with respect to the layer that has just been formed, after depositing of at least one droplet of binder, the source of radiation 190 is activated in order to cause the activation of the photoactivatable material, via photochemical and/or thermal decomposition of the photoinitiator and by radical reaction of the monomer or monomers and/or of the prepolymer or prepolymers and/or of the polymer or polymers.

Alternatively, the source of radiation 190 is activated after the nozzle or printing head 152 has finished its displacement with regards to the layer of powder that has just been formed, after the depositing of all of the binder to be placed on the layer of powder.

The binding activator binds the powder, for example by crosslinking in the chosen regions of the layer 19.

In this example, the color of each pixel of the layer 19 is defined in particular by the color of the binding activator or of the mix of binding activators sprayed on this pixel.

Once the layer 19 is formed, displacement assembly 160 is controlled in order to separate the previously formed layer 19 from the nozzle or printing head 152.

Another layer of powder is applied onto the previous layer by the member for dispensing powder 166.

The preceding operations are repeated in order to add the different layers 19 on each other.

Once all of the layers 19 of the three-dimensional object are formed, the powder not bound, present in the areas devoid of binding activator is removed from the three-dimensional object 10. The three-dimensional object 10 is as such cleaned.

According to the invention, at least one binding activator is applied onto the selected areas of several layers 19, and in certain cases all of the layers 19 are formed in order to construct in an additive manner the structured cosmetic composition within the three-dimensional object 10.

It is as such possible to construct three-dimensional objects 10 that comprise or are formed from a cosmetic composition having chosen and complex forms, different compositions and appearances according to the area, shadings of appearance and composition, through the simple local control of the binding activator to be added in each area of a given layer 19 of the three-dimensional object 10.

In an alternative (not shown), the apparatus 150 comprises an additional printing head, able to spray one or a plurality of inks contained in at least one printing cartridge.

The ink or inks are sprayed onto each pixel, as a complement to the linking activator and optionally to the photoactivatable material sprayed on this pixel. The color of each pixel is therefore obtained by the mix of the binding activator or activators sprayed onto the pixel, optionally of the photoactivatable material and by the ink or inks sprayed onto the pixel.

The color of each pixel of each layer 19 of the cosmetic composition can therefore be predefined, and obtained precisely on the cosmetic composition manufactured by the method according to the invention.

In particular, each region of the cosmetic composition can be manufactured with a color chosen by the user. For example, the apparatus 150 can comprise a color analysis device, in particular a spectrophotometer able to determine the characteristic data of a color chosen by the user, taken for example from a range of colors or from an accessory such as a piece of clothing.

The spectrophotometer is for example of the type marketed by "X-Rite".

The apparatus 150 is then able to use the data to construct a cosmetic composition that has at least one region of color similar to that determined by the color analysis device, either by using a mix of suitable binding activators, or by using a mix of inks contained in a printing cartridge.

In an alternative, at least one binding activator added in at least one layer 19 is intended to form a substrate 18 of the cosmetic composition which is a part of the three-dimensional object 10. Advantageously the substrate 18 formed as such cannot be restored after solidification, conversely to the cosmetic composition.

Examples of activators for the substrate 18 are binders containing a polymer soluble in alcohols, in water and/or in cetones, such as polyvinyl butyral (PVB), polyvinyl acetate (PVAC) or polyvinyl alcohol (PVAL).

Alternatively, these binders are adhesives or thermosetting materials.

The binding activator intended to form the substrate 18 is then sprayed using a specific nozzle or printing head 152.

In this alternative, at least one partially liquid binding activator layer intended for forming the substrate is deposited during the forming of the three-dimensional object.

Onto at least one layer of powder is added either exclusively a first binding activator intended to form a region of the substrate, or a second binding activator intended to form a region of the cosmetic composition and a first binding activator intended to form a region of the substrate.

In this case, the apparatus 150 comprises at least one container 154 for the packaging of the substrate material and a conveying assembly 156 of the substrate material between the container 154 and the nozzle or printing head 152.

The control unit 162 is able to determine if the substrate material must be added at a given position of the nozzle or printing head 152, as a complement or as a replacement for a cosmetic material.

The binding activator intended to form a region of the substrate is for example a polymer, in particular a thermoplastic polymer or a non-recoverable photoactivatable polymer, taken from a family such as defined hereinabove.

The crosslinked substrate material under the effect of the illumination and/or the heating generated by the source 190 in order to form the substrate 18.

In a particular example, the substrate material is formed of a non-recoverable photoactivatable material such as defined hereinabove, which crosslinks during the forming of the three-dimensional object 10. The cosmetic composition 12 can then contain at least one recoverable photoactivatable material or not contain one.

In another alternative, the cosmetic composition defines at least one central hollow region containing loose powder devoid of a binding activator, encapsulated in a region formed of bound powder.

Advantageously, the manufacturing method according to the invention is implemented for the creation of prototypes of three-dimensional objects comprising or formed of a structured cosmetic composition.

Alternatively, the manufacturing method according to the invention is implemented for the creation in production of finished products, for example in a factory or in a store.

The invention claimed is:

1. A method for the additive manufacture of a three-dimensional object comprising or forming a cosmetic composition, the method comprising the following steps:
   (a) forming a powder layer comprising at least one cosmetic powder;
   (b) supplying a photoactivatable material on at least a first region of the layer;
   (c) illuminating at least the first region of the layer to activate the photoactivatable material;
   (d) forming an additional powder layer comprising at least one cosmetic powder, the additional layer at least partially covering the previous layer;
   (e) supplying a photoactivatable material on at least a second region of the additional layer;
   (f) illuminating at least the second region of the additional layer to activate the photoactivatable material;
   (g) repeating steps (d) to (f) until the three-dimensional object is formed,
   the cosmetic composition comprised in the three-dimensional object or forming the three-dimensional object being recoverable after the three-dimensional object is formed.

2. The method according to claim 1, wherein the photoactivatable material comprises a photoinitiator and a photocrosslinkable compound suitable for activation by the photoinitiator.

3. The method according to claim 2, wherein the photocrosslinkable compound comprises at least one monomer, and/or at least one prepolymer and/or at least one polymer.

4. The method according to claim 1, wherein the photoactivatable material is deposited in liquid form via a nozzle or printing head on the first region and/or on the second region.

5. The method according to claim 4, wherein depositing the photoactivatable material comprises positioning the nozzle or printing head in a succession of given positions on the first region and/or on the second region,
and, in each given position, depositing a given quantity of photoactivatable material, illuminating the photoactivatable material deposited in the given position, and moving the nozzle or printing head to another given position on the first region and/or on the second region.

6. The method according to claim 1, wherein the illumination comprises positioning an advantageously coherent light source in regard to a succession of given points on the first region and/or on the second region, and for each given point, illuminating the photoactivatable material in the given position, and then moving the light source to another given position on the first region and/or on the second region.

7. The method according to claim 1, wherein the photoactivatable material is included in or forms a binding activator intended to bind at least one cosmetic powder.

8. The method according to claim 1, wherein at least one layer comprises a photoactivatable substrate material suitable for forming a substrate of the cosmetic composition, the substrate being non-recoverable, the method comprising illuminating the photoactivatable substrate material to form at least a part of the substrate.

9. The method according to claim 1, wherein step (a) comprises the formation of the powder layer comprising the at least one cosmetic powder, wherein the powder layer is a plane powder layer;
the method comprising applying a powder binding activator and binding the powder in at least a first region of the powder layer;
step (e) comprising the formation of an additional plane powder layer comprising at least one cosmetic powder, the additional layer covering the previous layer;
the method comprising applying a powder binding activator on at least a second region of the additional powder layer,
the photoactivatable material being advantageously contained in the binding activator.

10. The method according to claim 1, wherein a first binding activator supplied in the application step has a first color, a second binding activator supplied in the application step having a second color, the cosmetic composition formed comprising the first binding activator and the second binding activator on the same layer or on different layers.

11. The method according to claim 1, comprising a step for depositing at least one ink from a printing cartridge on at least one powder layer formed in step (a) or in step (d).

12. The method according to claim 1, wherein the cosmetic powder contains fillers, pigments, colorants, polymers and/or fibers.

13. The method according to claim 1, wherein the three-dimensional object is chosen from a make-up powder, a hybrid powder, or a wet powder, a deodorant and/or antiperspirant powder product, a solid shampoo or soap powder.

14. An apparatus for the additive manufacture of a three-dimensional object comprising or forming a cosmetic composition, the apparatus comprising:
a substrate surface;
an assembly for forming successive layers comprising at least one cosmetic material and, for at least one layer, a photoactivatable material;
a source for illuminating the photoactivatable material;
a control unit, suitable for controlling the formation assembly, and the illumination source to perform the following steps:
(a) forming a powder layer comprising at least one cosmetic powder;
(b) supplying a photoactivatable material on at least a first region of the layer;
(c) illuminating at least the first region of the layer to activate the photoactivatable material;
(d) forming an additional powder layer comprising at least one cosmetic powder, the additional layer at least partially covering the previous layer;
(e) supplying a photoactivatable material on at least a second region of the additional layer;
(f) illuminating at least the second region of the additional layer to activate the photoactivatable material;
(g) repeating steps (d) to (f) until the three-dimensional object is formed,
the cosmetic composition comprised in the three-dimensional object or forming the three-dimensional object being recoverable after the three-dimensional object is formed.

15. The apparatus according to claim 14, wherein the light source is chosen from a lamp and a laser.

16. The apparatus according to claim 15, wherein the formation assembly comprises at least one nozzle or printing head intended to dispense the photoactivatable material and/or at least one powder binding activator, the light source being suitable for moving in conjunction with the nozzle or printing head.

17. The method according to claim 2, wherein the photoactivatable material is deposited in liquid form via a nozzle or printing head on the first region and/or on the second region.

18. The method according to claim 3, wherein the photoactivatable material is deposited in liquid form via a nozzle or printing head on the first region and/or on the second region.

19. The method according to claim 2, wherein the illumination comprises positioning an advantageously coherent light source in regard to a succession of given points on the first region and/or on the second region, and for each given point, illuminating the photoactivatable material in the given position, and then moving the light source to another given position on the first region and/or on the second region.

20. The method according to claim 3, wherein the illumination comprises positioning an advantageously coherent light source in regard to a succession of given points on the first region and/or on the second region, and for each given point, illuminating the photoactivatable material in the given position, and then moving the light source to another given position on the first region and/or on the second region.

* * * * *